United States Patent [19]

Yeaw

[11] 4,379,848

[45] Apr. 12, 1983

[54] METHOD OF ANALYZING AN AQUEOUS LIQUID FOR HEXACYANOFERRATES

[75] Inventor: David C. Yeaw, Rochester, N.Y.

[73] Assignee: Eastman Kodak Company, Rochester, N.Y.

[21] Appl. No.: 306,621

[22] Filed: Sep. 28, 1981

[51] Int. Cl.³ .................................................. G01N 31/22
[52] U.S. Cl. ....................................... 436/84; 436/109; 436/53; 422/82
[58] Field of Search ........................ 23/230 R, 230 M; 252/408; 436/53, 109; 422/82

[56] References Cited

PUBLICATIONS

*Chemical Abstracts*, vol. 94, 1981, No. 128425a.
Nebergall, William H. et al., *General Chemistry*, D. C. Heath and Co., Lexington, Mass., 1972, pp. 229, 901.
*Chemical Abstracts*, vol. 85, 1976, p. 474, Abstract No. 85:28154g, Yogo et al., "Spectrophotometric Determination of Ferro- and Ferricyanide Ions with 1,10--phenanthroline".
*Chemical Abstracts*, vol. 73, 1970, p. 212, Abstract No. 69609e, Vail et al., "Photometric Determination of Ferrocyanides".
American Cyanamid Company, *Cyanamid's Nitrogen Chemicals Digest*, N.Y., 1953, vol. VII, *The Chemistry of the Ferrocyanides*, p. 48.
Cotton and Wilkinson, *Advanced Inorganic Chemistry*, N.Y., Interscience Publishers, 1966, pp. 860–861.
*Chemical Abstracts*, vol. 88, 1978, p. 619, Abstract No. 88:98638d, Meditsch, "Semiquantitative Determination of Ferrocyanides".
*Chemical Abstracts*, vol. 78, 1978, p. 252, Abstract No. 140022u, Abramkina et al., "Determination of Ferro- and Ferricyanides in Waste Waters of the Leningrad Motion Picture Copying Plant".

*Primary Examiner*—Michael S. Marcus
*Attorney, Agent, or Firm*—David F. Janci

[57] ABSTRACT

Colorimetric analysis for the presence or concentration of hexacyanoferrates in an aqueous liquid is carried out by forming a colored indicator compound which is soluble therein. The analysis is based on the use of a cobaltic complex of tris-1,10-phenanthroline or tris-2,2'-bipyridyl as an analytical reagent.

16 Claims, 1 Drawing Figure

METHOD OF ANALYZING AN AQUEOUS LIQUID FOR HEXACYANOFERRATES

BACKGROUND OF THE INVENTION

1. Field of the Invention

The invention relates to a method of detecting and/or quantitatively analyzing hexacyanoferrates in an aqueous liquid.

As used herein, the term "hexacyanoferrates" encompasses both the hexacyanoferrate (II) ion (also referred to as ferrocyanide) and the hexacyanoferrate (III) ion (also referred to as ferricyanide).

2. Description Relative to the Prior Art

Hexacyanoferrates are widely used in many industries. They are used in the manufacture of blueprints, chemicals, detergents, textile dyes, mirrors, mortar, pesticides, pigments, and rubber. They are also used in case hardening, electroplating, photographic processing, mineral dressing, steel pickling, chemotherapy and the prevention of corrosion.

In such industries efforts are made to closely control the concentration of hexacyanoferrates in effluent streams because of environmental considerations. In effecting such control, it is desirable to be able to detect hexacyanoferrates, and in some instances to determine their concentration, in an aqueous liquid, and various methods are known for accomplishing this.

One group of such methods involves contacting a sample of the aqueous liquid with reagents which will react with hexacyanoferrates in acidic solutions to produce indicator compounds comprising blue precipitates such as Turnbull's Blue, Prussian Blue, and Berlin Blue. The reagents used are solutions containing ferric and/or ferrous ions. In acidic solutions these ions react with hexacyanoferrates to form complex salts (the blue precipitates). Such reactions are generally described, for example, in Cotton and Wilkinson, *Advanced Inorganic Chemistry*, N.Y., Interscience Publishers, 1966, pp. 860–1.

Descriptions of the use of such reactions to detect and quantitatively analyze hexacyanoferrates have also been published. For example, *Chemical Abstracts*, Vol. 88, 1978, p. 619, Abstract No. 88:98638d, Meditsch, "Semi-quantitative determination of ferrocyanides," describes a method of detecting ferrocyanides by reaction with ferric salts impregnated in a filter paper test strip to form a precipitate of Prussian Blue (a complex ferric ferrocyanide salt). The color intensity of the precipitate is visually compared to similarly prepared standards in order to determine the concentration of ferrocyanide. Such a method suffers from lack of precision and sensitivity and from interference from extraneous precipitates which can form, depending upon the presence of other ions in the liquid being tested. For example, sulfur precipitates will also be formed if this method is used to test an aqueous effluent that contains thiosulfate ions, such as would commonly be encountered in photographic processing operations utilizing a ferricyanide bleach bath and a thiosulfate fixing bath. Such a method is also not readily applicable to an automated process for monitoring hexacyanoferrate concentration.

*Chemical Abstracts*, Vol. 78, 1978, p. 252, Abstract No. 140022u, Abramkina et al, "Determination of ferro- and ferricyanides in waste waters of the Leningrad Motion Picture Copying Plant," describes a method of quantitatively analyzing hexacyanoferrates in waste water by contacting a sample of the water with ferrous sulfate to form a precipitate of Turnbull's Blue (a complex ferrous ferricyanide salt) through reaction with ferricyanide and by contacting the sample with ferric chloride to form a precipitate of Berlin Blue (a complex ferric ferrocyanide salt) through reaction with ferrocyanide. The spectral densities of the precipitates of Turnbull's Blue and Berlin Blue are then measured in solution colorimetrically in order to determine the hexacyanoferrate concentrations. This method has the advantage over the filter paper method of being adaptable to automated on-line concentration monitoring through use of a flow cell colorimeter. The method suffers, however, from lack of sensitivity, accuracy, and precision and from interference by other precipitates (e.g., sulfur). Since the colored indicator compounds formed are themselves precipitates, they, along with any extraneous precipitates, tend to coat the flow-analysis apparatus, necessitating a complicated and expensive cleaning procedure. Furthermore, if the concentration of hexacyanoferrates in the water being analyzed is high enough (approximately 50 mg/L) the indicator precipitates will begin to clump together in the flow cell and cause the colorimeter measurements to become highly inaccurate (e.g., in many such cases the colorimeter readings will indicate much lower concentrations of hexacyanoferrates than are actually present in the sample).

Some of these problems can be avoided by other known methods of hexacyanoferrate analysis. *Chemical Abstracts*, Vol. 85, 1976, p. 474, Abstract No. 85:28154g, Yogo et al, "Spectrophotometric determination of ferro- and ferricyanide ions with 1,10-phenanthroline," describes a method of analyzing hexacyanoferrates in water at a pH of 2 to 4 by heating the water in the presence of a mercury catalyst and 1,10-phenanthroline and measuring the resultant spectral density of the solution. *Chemical Abstracts*, Vol. 73, 1970, p. 212, Abstract No. 69609e, Vail et al, "Photometric determination of ferrocyanides," describes a method of analyzing ferrocyanide in water at a pH of 4 by heating the water in contact with 2,2'-bipyridyl or 1,10-phenanthroline, formaldehyde, and an acetate buffer and measuring the resultant spectral density of the solution. The indicator compounds formed in these methods are the ferric and ferrous complexes of 1,10-phenanthroline and 2,2'-bipyridyl. Such complexes are soluble in aqueous liquids, and these methods avoid, therefore, the problems associated with the precipitating indicators formed in the other methods described above. Other problems remain, however, such as the likelihood that extraneous precipitates will be formed and interfere with the density measurements (e.g., if thiosulfate ions are present in a solution at a pH of 4 or less, sulfur precipitates can form). In addition, the heating with acid involved in the methods described in these two publications results in the decomposition of hexacyanoferrates to form ferrates and cyanides, whereafter the ferrate ions complex with the bipyridyl or phenanthroline, while the cyanide comes off as a gas which must be carefully handled and disposed of without significant escape into the environment.

Clearly, it would be desirable to have available a method of detecting and quantitatively analyzing hexacyanoferrates which: (1) exhibits high sensitivity, precision, and accuracy; (2) involves the formation of an indicator compound that is water-soluble; (3) avoids the formation of extraneous precipitates such as sulfur; (4)

does not produce cyanide gas as a by-product; and (5) can be practically used in an automated, on-line, continuous-flow analytical system. The present invention provides such a method through the use of cobaltic complexes of tris-1,10-phenanthroline or tris-2,2'-bipyridyl which form water-soluble indicator complexes with hexacyanoferrates.

In regard to such complexes, it should be noted that American Cyanamid Company, *Cyanamid's Nitrogen Chemicals Digest*, N.Y., 1953, Vol. VII, *The Chemistry of the Ferrocyanides*, p. 48, briefly indicates that the cobaltous complex of ferrocyanide and tris-phenanthroline can exist as a colored precipitate in acidic liquids, but the publication describes no analytical method of using such a complex and does not describe cobaltic phenanthroline complexes or any uses thereof; i.e., its disclosure relates solely to a cobaltous complex rather than a cobaltic complex.

SUMMARY OF THE INVENTION

The present invention provides a method which can be used for detecting or for quantitatively analyzing hexacyanoferrates in an aqueous liquid.

For simply detecting hexacyanoferrates in an aqueous liquid, the method comprises two steps. First, an alkaline reaction system is formed comprising the aqueous liquid and a cobaltic complex of tris-1,10-phenanthroline or tris-2,2'-bipyridyl. Second, the reaction system is acidified to an acid pH to effect a detectable change in the spectral density thereof indicative of the presence of hexacyanoferrates in the aqueous liquid.

For quantitatively analyzing hexacyanoferrates in an aqueous liquid, the method comprises a third step in addition to the two just described. Such method takes advantage of the fact that the spectral density change effected by the acidification of the reaction system is in proportion to the concentration of hexacyanoferrates in the aqueous liquid. The third step comprises measuring the spectral density of the acidified reaction system to determine the concentration of hexacyanoferrates in the aqueous liquid.

DESCRIPTION OF PREFERRED EMBODIMENTS

Figure 1:
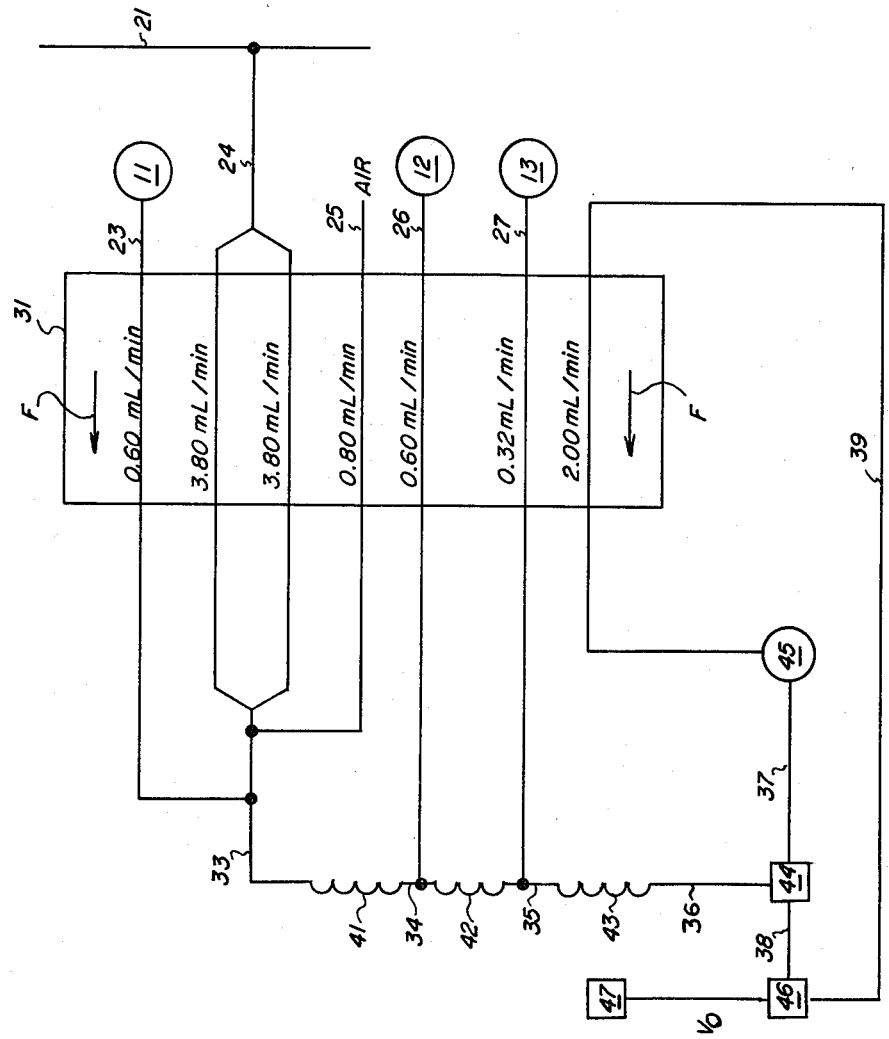
FIG. 1 is a block diagram illustrating the design and operation of a continuous-flow analytical system adapted to practice a preferred embodiment of the inventive method. It is described in more detail in the Example in the Description of Preferred Embodiments.

In practicing the method of the invention it is desirable (but optional) to include in the method, prior to the previously described first step, an oxidizing treatment of the aqueous liquid analyte (i.e., the aqueous liquid being analyzed) if the object of the practice is to determine:

(1) the combined concentration of all hexacyanoferrates in the analyte;

(2) the concentration of ferrocyanide in an analyte known to contain no significant amount of ferricyanide; or (3) the concentration of ferricyanide in an analyte known to contain no significant amount of ferrocyanide.

The purpose of this oxidizing treatment is twofold—to oxidize ferrocyanide in the analyte to ferricyanide and to oxidize any thiosulfate ions in the analyte to sulfate ions.

The advantage in oxidizing ferrocyanide to ferricyanide is that, during the acidification step in the method, ferricyanide produces a more marked and more consistently repeatable color change (i.e., change in spectral density) than does ferrocyanide. Therefore, if it is not an object of a particular practice of the method to be able to make separate determinations of ferrocyanide and ferricyanide concentrations, it is preferable to convert all ferrocyanide to ferricyanide before forming the reaction system.

The advantage in oxidizing thiosulfate ions to sulfate ions relates to the previously mentioned tendency of thiosulfate ions to form sulfur precipitates in acidic solutions. When an aqueous liquid is brought to a pH of 4 or less, thiosulfate in the liquid tends to be converted in part to sulfur, which precipitates out of the liquid, coating the analytical apparatus and generally interfering with the measurement of intended spectral density changes in the liquid. While this problem is avoided in some preferred embodiments of the inventive method, wherein the pH of the reaction system is controlled in the acidification step so as not to be allowed to go as low as 4, it is alternatively avoided by this initial oxidizing treatment of the analyte to convert thiosulfate ions to sulfate ions. Sulfate ions will not undergo a sulfurization conversion (i.e., will not form sulfur precipitates) during the acidification step, and, therefore, the pH need not be so closely controlled during the acidification if the oxidizing treatment has been carried out previously.

The oxidizing treatment comprises contacting the aqueous liquid analyte with an oxidizing agent. The oxidizing agent is any strong oxidizing agent which will convert ferrocyanide to ferricyanide and thiosulfate to sulfate without interfering with the spectral density changes intended to be effected by the subsequent steps of the analytical method. Examples of preferred oxidizing agents are potassium persulfate and hydrogen peroxide.

During the oxidizing treatment it is preferable that the analyte have an alkaline pH while being contacted with the oxidizing agent. Again, the purpose is twofold. First, since in the subsequent step of forming the reaction system, the system must be alkaline for the analytical method to operate properly, it is convenient to assure alkalinity at this prior point in time. Second, if the analyte is alkaline during the oxidizing treatment, the possibility of decomposing the hexacyanoferrates and forming extraneous precipitates therefrom is avoided. If the analyte were not alkaline during the oxidation and other metal ion impurities were present in the analyte, it is possible that these metal ion impurities would form cyanate salt precipitates with the cyanide portions of the hexacyanoferrates, thus lessening the sensitivity, accuracy, and precision of the analytical method. Of course, if the analyte is alkaline initially, there will be no problem. If it is not, then it is desirable to adjust the pH of the analyte by mixing a base compound with the analyte, e.g., a compound such as sodium hydroxide or potassium hydroxide, during or before the oxidizing treatment.

After the oxidizing treatment (or as the initial step in the method, if no oxidizing treatment has been carried out), the alkaline reaction system, comprising the aqueous liquid analyte and an analytical reagent comprising a cobaltic complex of tris-1,10-phenanthroline or tris-2,2'-bipyridyl, is formed. This is accomplished by bringing the analyte and the reagent together in a chamber or vessel where they can mix and react with each other spontaneously.

The analytical reagent can be conveniently referred to as a cobaltoin reagent. Its active component is a complex of a $Co^{3+}$ ion with three 1,10-phenanthroline groups or with three 2,2'-bipyridyl groups. These complexes are represented by the shorthand formulas $Co(phen)_3^{3+}$ and $Co(bipy)_3^{3+}$ respectively.

The cobaltoin reagent is easily prepared by dissolving 1,10-phenanthroline or 2,2'-bipyridyl in a water-miscible organic solvent and then mixing with that solution an aqueous solution of cobaltous or cobaltic salt to form the reagent spontaneously.

The water-miscible organic solvent is chosen from a wide variety of solvents in which the 1,10-phenanthroline or 2,2'-bipyridyl has good solubility. Examples of preferred solvents for this purpose are acetone and the lower alcohols, such as methanol, ethanol, propanol, and butanol.

The cobaltous or cobaltic salt is chosen from salts which are water-soluble, such as the halides, sulfates, and nitrates of cobalt. Specific examples are cobaltous chloride, cobaltous bromide, cobaltous nitrate, cobaltous sulfate, cobaltic fluoride, and cobaltic sulfate.

If hexacyanoferrates are present in the analyte, they will react spontaneously, upon formation of the alkaline reaction system, with the $Co(phen)_3^{3+}$ or $Co(bipy)_3^{3+}$ to form intermediate complexes having structures which are presently undetermined and not colorimetrically detectable.

If the analyte was not alkaline initially and was not made alkaline by the optional oxidizing treatment, the reaction system is made alkaline by incorporation of a base (e.g., sodium hydroxide or potassium hydroxide) into the system in order to enable the formation of the intermediate complexes. In acidic solutions $Co(phen)_3^{3+}$ and $Co(bipy)_3^{3+}$ would not react with hexacyanoferrates to form the desired intermediate complexes. It is preferred that the alkaline reaction system have a pH of at least 10 in order to assure full spontaneous formation of the desired intermediate complexes with virtually all hexacyanoferrates present in the analyte.

The next step of the inventive method is the acidification of the alkaline reaction system to effect a change in spectral density (e.g., a change in color) of the reaction system in proportion to the concentration of hexacyanoferrates in the aqueous liquid analyte. The change in spectral density is caused by the formation of final indicator complexes from the intermediate complexes by acidification. Acidifying the alkaline reaction system (i.e., changing its alkaline pH to an acidic pH) causes a change in the structure of the intermediate complexes, whereby colored indicator complexes are formed, each of which comprises one hexacyanoferrate ion in association with one cobaltic tris-1,10-phenanthroline complex or with one cobaltic tris-2,2'-bipyridyl complex.

These final indicator complexes are water-soluble and remain in solution in the acidified reaction system. They are blue in color and thereby impart a blue coloration to the reaction system.

The acidification is preferably carried out by mixing an acid with the alkaline reaction system. Any inorganic or organic acid is appropriate for this purpose, but in order to be assured that unwanted side reactions (e.g., with impurities that may be present in the analyte) are avoided, it is preferable to avoid using strong mineral acids or acids that are strong oxidants. A specific example of an acid used in some preferred embodiments of the invention is acetic acid.

The acid is preferably mixed with the alkaline reaction system in an amount sufficient to bring the reaction system to a pH of 6 or less, in order to assure full formation of the colored indicator complexes. More preferably, the pH is not allowed to go as low as 2, so as to avoid possible side reactions between the acid and extraneous compounds present in the analyte or formed during previous steps.

In some preferred embodiments of the inventive method the alkaline reaction system is acidified to a pH greater than 4 and less than or equal to 6. This is especially useful, for example, in situations where the analyte contains thiosulfate ions and the previously described optional oxidizing treatment has not been carried out, i.e., the thiosulfate has not been converted to sulfate. In such situations, keeping the pH above 4 will preclude significant formation of undesirable sulfur precipitates from the thiosulfate ions.

After the acidification has been carried out, and if the purpose of practicing the method is simply to determine whether any hexacyanoferrate ions were present in the analyte, the acidified liquid reaction system is visually observed to determine whether the liquid has taken on a blue coloration. If so, it can be concluded that some hexacyanoferrate ions were present in the analyte.

When a determination of the concentration of hexacyanoferrates in the analyte is desired, the spectral density of the acidified liquid reaction system is measured (e.g., colorimetrically) to determine the degree of spectral density change caused by the formation of the final indicator complexes. Hexacyanoferrate concentration can then be calculated, because the degree of spectral density change is in proportion to such concentration.

Apparatus and procedures for colorimetric determinations are commonly known and available. Colorimetric measurements in a liquid flow cell are preferred, because: (1) the final indicator complexes remain dissolved in the acidified reaction system; (2) the flow cell path length can be varied to achieve the range of sensitivity desired; and (3) flow cells are particularly adaptable to on-line, continuous-flow analytical methods, which are themselves particularly adaptable to automated analytical systems. For example, in one automated analytical system, apparatus is designed to sample effluent from an ion exchange column being used to remove ferrocyanide from a photographic fix-wash solution. The apparatus treats the samples in accordance with the inventive method. The system is designed to put out an electrical signal when the spectral density measured by the colorimeter reaches a predetermined level. This signal activates solenoid valves to initiate regeneration of the ion exchange resin in the column before it can become exhausted and allow objectionable amounts of ferrocyanide to escape with the effluent. Virtually any amount of ferrocyanide that is considered objectionable can be detected by this method; i.e., very low concentrations of ferrocyanide can be determined by equipping the colorimeter with a flow cell of sufficient length for this purpose.

As indicated previously, if it is an object of a particular practice of the inventive method to make separate determinations of ferrocyanide and ferricyanide concentrations in a single analyte, the previously described oxidizing treatment is not used, so that ferrocyanide will not be converted to ferricyanide. The complexes formed by the cobaltoin reagent with ferrocyanide in accordance with the inventive method exhibit maximum spectral absorptivity (and maximum spectral density) at different wavelengths in the electromagnetic spectrum than do the analagous complexes with ferricyanide, and these wavelengths can be easily determined by scanning spectrophotometry. Therefore, by separately measuring the spectral density of the acidified reaction system at these various wavelengths of maximum absorptivity, one can then determine the separate concentrations of ferrocyanide and ferricyanide in the analyte.

The following example is presented to further illustrate the practice of a preferred embodiment of the inventive method.

EXAMPLE

Continuous Flow Quantitative Analysis of Hexacyanoferrates in an Aqueous Liquid The inventive method was practiced in a continuous-flow analytical apparatus, the design and operation of which is represented by FIG. 1 in the drawing.

An alkaline oxidizing reagent was prepared by dissolving 40 grams of potassium persulfate and 20 grams of sodium hydroxide in water to make one liter. Referring to FIG. 1, this alkaline oxidizing reagent was placed in supply tank 11.

Cobaltoin reagent was prepared as follows. 10 grams of tris-1,10-phenanthroline were dissolved in 50 ml of methanol in a dry, one liter bottle. 4.7 grams of $CoSO_4.7H_2O$ were added to the bottle. Water was added to fill the bottle while stirring to assure that all solids dissolved. The cobaltoin reagent was placed in supply tank 12.

An acidifying reagent comprising 2.0 N acetic acid was prepared by mixing 114 mL of glacial acetic acid with water to make one liter. The acidifying reagent was placed in supply tank 13.

Standard aqueous analyte solutions containing known concentrations of silver bromide, ammonium thiosulfate, and sodium ferrocyanide were prepared. 10 different solutions were prepared. All of them contained 60 mg of thiosulfate ions per liter and 21 mg of silver ions per liter, but each contained a different known concentration of ferrocyanide ions ranging from 1 mg/L to 100 mg/L. These solutions were intended to approximate common effluent from a photographic fix-wash bath (i.e., the rinsing bath that is used immediately after the fixing bath in a common photographic process). The inventive method was practiced while these solutions were successively passed through conduit 21.

In operation the analytical apparatus drew oxidizing reagent, standard aqueous analyte solution, air, cobaltoin reagent, and acidifying reagent through flexible plastic conduits 23, 24, 25, 26, and 27 respectively by means of peristaltic pump 31 (comprising a commonly used arrangement of rollers and a platen for squeezing fluids through flexible conduits by peristaltic action). The flow rate through each conduit was as indicated in FIG. 1, and the direction of flow through the pump was as indicated by arrows F.

Alkaline oxidizing reagent, analyte, and air were brought together in conduit 33 and then passed through thirty-turn mixing coil 41. The air helped the reagent and analyte to mix and react. Ferrocyanide ions in the analyte were oxidized to ferricyanide, and thiosulfate ions were oxidized to sulfate. The sodium hydroxide imparted an alkaline pH to the mix.

The mix then passed through conduit 34, where it was brought together with cobaltoin reagent to form an alkaline reaction solution, which then passed through fifteen-turn mixing coil 42 where intermediate complexes were formed.

The alkaline reaction solution then passed through conduit 35, where it was contacted with the acidifying reagent, which brought the reaction solution to a pH of 4.8 to 5.0, and then through thirty-turn mixing coil 43, where the final indicator complexes formed and remained dissolved in the acidified reaction solution. These final indicator complexes comprised ion pairs of ferricyanide and cobaltic tris-1,10-phenanthroline having maximum optical absorptivity at a wavelength of about 640 nanometers.

The acidified reaction solution then passed through conduit 36 and through a debubbling apparatus 44, which removed the air (initially added to aid mixing) and part of the solution, sending them to drain 45 through conduit 37. The remaining solution passed through conduit 38 to colorimeter 46, where its spectral density was continuously measured, and then to drain 45 through conduit 39 (at a rate of 2 mL/min. under influence of pump 31).

Colorimeter 46 was equipped with a 15 mm pathlength flow cell and optical filters, so that the spectral density measurements continuously made of solution in the flow cell were measurements of the transmission density of the solution to light having a wavelength of about 640 nanometers (the wavelength of maximum spectral absorptivity for the only complexes of interest formed in this particular application of the inventive method). An electrical signal having a voltage $V_o$, which was proportional to the density measured and proportional to the concentration of hexacyanoferrates in the analyte, was sent to strip chart recorder 47, which was electrically connected to colorimeter 46 to thereby plot voltage versus time.

The plot of voltages was found to be a highly precise, accurate and reliable indicator of the 1 to 100 mg/L hexacyanoferrate concentrations in the various standard aqueous analyte solutions run through conduit 21. Standard deviation of the calculated concentration values from the known actual values was ±4%. No precipitates formed in acidified reaction solution; so there was no problem of coating of the flow cell. No toxic gases were given off during the process. Good sensitivity, accuracy, and precision can be achieved at lower levels of hexacyanoferrate concentration by increasing analyte to reagent volume ratios and/or increasing flow cell path length.

The invention has been described in detail with particular reference to preferred embodiments thereof, but it will be understood that variations and modifications can be effected within the spirit and scope of the invention.

What is claimed is:
1. A method for detecting hexacyanoferrates in an aqueous liquid, the method comprising the steps of:
   (a) forming an alkaline reaction system comprising the aqueous liquid and a cobaltic complex of tris-1,10-phenanthroline or tris-2,2'-bipyridyl;
   (b) acidifying the reaction system to effect a detectable change in the spectral density thereof indica- tive of the presence of hexacyanoferrates in the aqueous liquid; and (c) observing the detectable change indicative of the presence of hexacyanoferrates.

2. A method for determining the concentration of hexacyanoferrates in an aqueous liquid, the method comprising the steps of:

(a) forming an alkaline reaction system comprising the aqueous liquid and a cobaltic complex of tris-1,10-phenanthroline or tris-2,2'-bipyridyl;

(b) acidifying the reaction system to effect a change in the spectral density thereof in proportion to the concentration of hexacyanoferrates in the aqueous liquid; and (c) measuring the spectral density of the acidified reaction system to determine the concentration of hexacyanoferrates in the aqueous liquid.

3. The method of claims 1 or 2 wherein, prior to step (a), the aqueous liquid is contacted with an oxidizing agent to convert any ferrocyanide present in the aqueous liquid to ferricyanide.

4. The method of claim 3, wherein the oxidizing agent is potassium persulfate or hydrogen peroxide.

5. The method of claim 3, wherein the aqueous liquid has an alkaline pH while being contacted with the oxidizing agent.

6. The method of claim 5, wherein the aqueous liquid is made alkaline by mixing a base with the aqueous liquid.

7. The method of claim 6, wherein the base is sodium hydroxide or potassium hydroxide.

8. The method of claims 1 or 2, wherein the alkaline reaction system of step (a) has a pH of at least 10.

9. The method of claims 1 or 2, wherein the reaction system is made alkaline in step (a) by incorporating a base in the reaction system.

10. The method of claim 9, wherein the base is sodium hydroxide or potassium hydroxide.

11. The method of claims 1 or 2, wherein the alkaline reaction system is acidified in step (b) by mixing an acid with the alkaline reaction system.

12. The method of claim 11, wherein the acid is acetic acid.

13. The method of claims 1 or 2, wherein the alkaline reaction system is acidified in step (b) to a pH less than or equal to 6.

14. The method of claims 1 or 2, wherein the alkaline reaction system is acidified in step (b) to a pH greater than 2 and less than or equal to 6.

15. The method of claims 1 or 2, wherein the alkaline reaction system is acidified in step (b) to a pH greater than 4 and less than or equal to 6.

16. The method of claims 1 or 2, wherein the aqueous liquid contains thiosulfate ions.

* * * * *